United States Patent [19]

Greenwald

[11] 4,020,176
[45] Apr. 26, 1977

[54] HIGHLY FLUORINATED DIAZIDES AND PROCESS THEREFOR
[75] Inventor: Richard B. Greenwald, Lexington, Mass.
[73] Assignee: Polaroid Corporation, Cambridge, Mass.
[22] Filed: July 14, 1975
[21] Appl. No.: 595,488
[52] U.S. Cl. .............................. 260/349
[51] Int. Cl.² .................... C07C 117/00
[58] Field of Search ................... 260/349
[56] References Cited
UNITED STATES PATENTS

| 2,769,819 | 11/1956 | Sommers et al. | 260/349 |
| 3,122,570 | 2/1964 | Stansbury et al. | 260/349 |
| 3,232,958 | 2/1966 | Washburn | 260/349 |
| 3,719,713 | 3/1973 | Molloy et al. | 260/349 |

FOREIGN PATENTS OR APPLICATIONS

| 456,801 | 3/1928 | Germany | 260/349 |

OTHER PUBLICATIONS

Sidgwick, N. V. "The Org. Chem. of Nitrogen" Oxford Press, 1949 p. 367.
Noeller, "Chem. of Org. Compounds" W. B. Saunders Co., London, 1965, p. 292.

*Primary Examiner*—Lewis Gotts
*Assistant Examiner*—Cary Owens
*Attorney, Agent, or Firm*—Sybil A. Campbell

[57] ABSTRACT

This invention relates to highly fluorinated diazides of the formula $N_3CH_2(CF_2)_xCH_2N_3$ wherein $x$ is a positive integer from 2 to 12; to the preparation of these diazides by the reaction of excess sodium azide with a ditosylate of the formula $C_7H_7SO_3CH_2(CF_2)_x$-$CH_2O_3SC_7H_7$ wherein $x$ has the same meaning given above; and to the synthesis of highly fluorinated primary diamines of the formula $H_2NCH_2(CF_2)_xCH_2NH_2$ wherein $x$ has the same meaning given above by catalytic hydrogenation of said diazides.

6 Claims, No Drawings

HIGHLY FLUORINATED DIAZIDES AND PROCESS THEREFOR

BACKGROUND OF THE INVENTION

1. Field of the Invention

This invention relates to a new method of synthesizing highly fluorinated aliphatic primary diamines, to novel intermediates useful in the preparation thereof and to the preparation of said intermediates.

2. Description of the Prior Art

Most highly fluorinated amines and diamines have been prepared by lithium aluminum hydride reduction of the corresponding amides as described by B. S. Marks and G. C. Schweiker, J. Amer. Chem. Soc., 80, p. 5789 (1958) or by high pressure (1000 psi) catalytic hydrogenation of nitriles as described by E. T. McBee, P. A. Wiseman and G. B. Backman, Ind. and Eng. Chem., 39, p. 415 (1947). The former method often gives highly explosive reaction mixtures, while the latter is inconvenient and involves an additional dehydration step in the synthesis. Both methods proceed in only moderate yield.

Other procedures also have been proposed but have not been altogether successful because of the relatively inert nature of the highly fluorinated starting materials as compared to their hydrocarbon counterparts. As reported by B. S. Marks and G. C. Schweiker, ibid., previous attempts to employ 2,2,3,3,4,4-hexafluoropentane-1,5-di-p-toluenesulfonate with ammonia and aliphatic amines, such as methylamine and diethylamine, gave only tarry mixtures from which no amine could be isolated. In one instance, as reported by H.A. Brown and G. V. D. Tiers, J. Org. Chem., 22, p. 454 (1957), reaction of 1,1-di-H-hepta-fluorobutyl p-toluenesulfonate with aniline at 230° C. for 24 hours gave a 68% by weight yield of the desired amine, but reaction under similar conditions with ammonia and diethylamine gave only tars from which the desired products could not be isolated.

In one aspect, the present invention is concerned with a new method of preparing highly fluorinated aliphatic diamines. In another aspect, the present invention is concerned with novel intermediates useful in preparing said diamines and with the synthesis of said intermediates.

SUMMARY OF THE INVENTION

It is one object of the present invention to provide a novel method of preparing highly fluorinated alkyl diamines.

It is another object of the present invention to provide highly fluorinated alkyl diazides useful as intermediates in the preparation of highly fluorinated alkyl diamines.

It is a further object of the present invention to provide a method of synthesizing said intermediates.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

According to the present invention, it has been found that $\alpha, \omega$-di-p-toluenesulfonates of highly fluorinated alkanes readily react with sodium azide to give an almost quantitative yield of the corresponding diazides when hexamethylphosphoric triamide (HMPA) is employed as the reaction solvent. Azide formation was not observed when other solvents, such as, N,N-dimethylformamide, ethanol and acetonitrile were employed. The diazide obtained is then reduced directly to the corresponding diamine, preferably, by catalytic hydrogenation.

This reaction sequence is illustrated below wherein x represents a positive integer from 2 to 12.

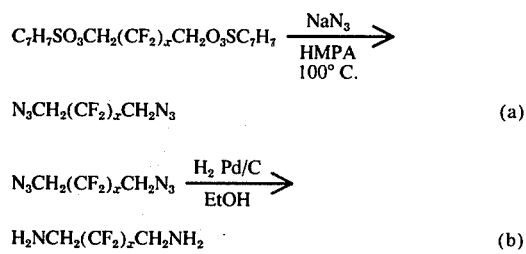

(a)

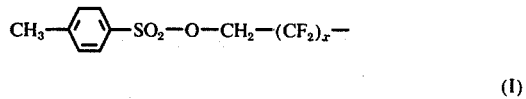

(b)

In carrying out the present invention, a tosylate having the formula

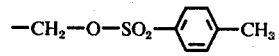

(I)

wherein $x$ is a positive integer from 2 to 12 is reacted with an excess of sodium azide in hexamethylphosphoric triamide at elevated temperature to yield the corresponding diazide having the formula $$N_3CH_2(CF_2)_xCH_2N_3 \qquad (II)$$

wherein $x$ has the same meaning given in Formula I above. At least 2 moles of sodium azide are used per mole of tosylate, and preferably, the sodium azide is used in a substantial excess, usually 4 to 5 moles per mole of ditosylate to achieve maximum yields. Though greater amounts of sodium azide may be employed, no further benefits are obtained. The temperature may range between about 50° and 115° C., but because of the longer reaction times required at the lower end of the range, the reaction is most conveniently carried out at a temperature between about 100° and 110° C. The diazides represented in Formula II comprise the novel intermediates of the present invention.

The diazides of Formula II may be reduced to the corresponding diamines having the formula

(III)

wherein $x$ has the same meaning given in Formula I above by chemical means, for example, by using lithium aluminum hydride in an inert organic solvent, such as ether, or preferably by catalytic hydrogenation. The latter reduction may be carried out at ambient temperature, e.g., 20°–30° C. by hydrogenation, generally at 15 to 50 psi H$_2$ in any organic solvent inert to hydrogenation, such as, acetic acid, ethyl acetate and peferably alcohols, e.g., ethanol, using Raney nickel, platinum or other hydrogenation catalyst. Particularly good results have been achieved with palladium on carbon. The catalytic reduction of azides is discussed by J. H. Boyer and F. C. Canter, Chem. Revs., Vol. 54, p. 1 (1954).

The following Examples are given to further illustrate the present invention and are not intended to limit the scope thereof.

EXAMPLE 1

Preparation of 2,2,3,3,4,4-hexafluoro-1,5-pentadiamine:

a. A mixture of 20.0 g. (0.038 mol) of 2,2,3,3,4,4-hexafluoropentane-1,5-di-p-toluenesulfonate, 10.0 g. (0.15 mole) of sodium azide, and 70 mls. of hexamethylphosphoric triamide was stirred and heated in an oil bath at 100°–110° C. for 19 hours. The mixture was cooled and about 300 mls. of water was added. The aqueous mixture was extracted three times with ether, washed twice with water, dried over MgSO$_4$, and evaporated in vacuo to leave 10.2 g. (99% by weight) of 2,2,3,3,4,4-hexafluoropentane-1,5-diazide as a pale yellow oil $\gamma_{max}^{neat}$ 2100 (s), 2150 (sh), 2210 (sh). NMR(CDCl$_3$)$\delta$2, 4–4.0 (m). The purity of the diazide was estimated by integrating the CH$_2$ multiplet against a small amount of aromatic resonance still present from unreacted tosylate, and was of the order of 90 ± 3%.

b. To a solution of 10.7 g. of 2,2,3,3,4,4,-hexafluoropentane-1,5-diazide in 60 mls. of absolute ethanol was added 1–2 g. of 10% palladium on carbon. The mixture was hydrogenated at 48 psi for 5 hours at ambient temperature, filtered, and the solvent evaporated under reduced pressure. Distillation of the residual oil gave 8.1 g. (90% by weight) of 2,2,3,3,4,4-hexafluoro-1,5-pentanediamine as a colorless oil, boiling range 65°–67° C. (0.7 mm), $\eta_D^{25}$ 1.373, which darkened slightly on standing. A sample in ethanol was treated with etheral HCl and the precipitate recrystallized from ethanol-ether, melting range 305°–310° C. (dec.).

Analysis for C$_5$H$_8$F$_6$N$_2$·2HCl: Calculated: C, 21.22; H, 2.81; N, 9.90; Found: C, 21.37; H, 3,46; N, 9.91.

EXAMPLE 2

Preparation of 2,2,3,3,4,4,5,5-octafluoro-1,6-hexanediamine:

a. 2,2,3,3,4,4,5,5-octafluoro-1,6-hexanediazide was prepared in 92 ± 3% by weight crude yield using the procedure of step (a) of Example 1 from 2,2,3,3,4,4,5,5-octafluorohexane-1,6-di-p-toluenesulfonate.

b. The title compound was prepared according to the procedure of step (b) of Example 1 in 87% by weight yield, boiling range 95°–98° C. (0.6 mm), melting range 44°–45° C. (melting range reported by E. T. McBee, P. A. Wiseman and G. B. Backman, ibid., 44°–45° C.).

The ditosylate starting materials are known and may be prepared in a conventional manner by reacting a diol, HOCH$_2$(CF$_2$)$_x$CH$_2$OH, with p-toluenesulfonyl chloride, for example, as reported by B. S. Marks and G. C. Schweiker, ibid. As an illustration 2,2,3,3,4,4,5,5-octafluorohexane-1,6-di-p-toluenesulfonate was prepared as follows:

To a solution of 100 g. (0.38 mol) of 2,2,3,3,4,4,5,5-octafluoro-1,6-diol in 500 mls. of dry pyridine cooled in an ice bath, was added 195.0 g. (1.0 mol) of p-toluenesulfonyl chloride in several portions with vigorous stirring. The temperature of the reaction was maintained at 30° C. or less until the end of the addition. After keeping the reaction chilled for a further 2 hours, it was allowed to equilibrate to room temperature and left overnight. The mixture was poured into 2 liters of cold 1N HCl and the precipitate collected. Trituration of the moist solid with methanol gave 188.2 g. (87% by weight) of the ditosylate as a white solid, melting range 134°–6° C.

The diols also are known in the art and may be prepared from a perfluoro acid, e.g., (CF$_2$)$_x$(COOH)$_2$ by forming an acid ester, e.g., by reacting the acid with ROH to give (CF$_2$)$_x$(COOR)$_2$ followed by reduction with lithium aluminum hydride to the diol, HOCH$_2$(CF$_2$)$_x$CH$_2$OH.

The product diamines also are known in the art and find utility in the production of polymeric materials.

Since certain changes may be made in the above compositions and processes without departing from the scope of the invention herein involved, it is intended that all matter contained in the above description should be interpreted as illustrative and not in a limiting sense.

What is claimed is:

1. A compound of the formula

wherein $x$ is a positive integer from 2 to 12.

2. A compound as defined in claim 1 wherein $x$ is 3.
3. A compound as defined in claim 1 wherein $x$ is 4.
4. A method which comprises reacting (a) one molar equivalent of a ditosylate having the formula

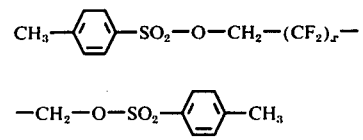

wherein $x$ is a positive integer from 2 to 12 and (b) at least 2 molar equivalents of sodium azide in hexamethylphosphoric triamide at elevated temperature to yield the corresponding diazide having the formula

wherein $x$ has the same meaning given above.

5. A method as defined in claim 4 wherein $x$ is 3.
6. A method as defined in claim 4 wherein $x$ is 4.

* * * * *